United States Patent [19]

Markström

[11] Patent Number: 5,490,410
[45] Date of Patent: Feb. 13, 1996

[54] PROCESS AND A DEVICE FOR MEASURING STATIC AND DYNAMIC FRICTION OF SHEET-SHAPED MATERIALS

[75] Inventor: Håkan Markström, Järfälla, Sweden

[73] Assignee: AB Lorentzen & Wettre, Kista, Sweden

[21] Appl. No.: 211,117

[22] PCT Filed: Sep. 21, 1992

[86] PCT No.: PCT/SE92/00651

§ 371 Date: Mar. 21, 1994

§ 102(e) Date: Mar. 21, 1994

[87] PCT Pub. No.: WO93/06455

PCT Pub. Date: Apr. 1, 1993

[30] Foreign Application Priority Data

Sep. 20, 1991 [SE] Sweden .................. 9102733

[51] Int. Cl.⁶ .................................................. G01N 19/02
[52] U.S. Cl. .................................................. 73/9; 73/7
[58] Field of Search .......................... 73/9, 7, 159, 815, 73/819, 826, 838, 841

[56] References Cited

U.S. PATENT DOCUMENTS

| | | |
|---|---|---|
| 1,668,593 | 5/1928 | Jones . |
| 3,098,377 | 7/1963 | Beauchamp . |
| 3,360,978 | 1/1968 | Shinn ................................... 73/9 |
| 5,097,696 | 3/1992 | Le Compagnon ..................... 73/9 |

FOREIGN PATENT DOCUMENTS

| | | | |
|---|---|---|---|
| 0491234 | 6/1992 | European Pat. Off. . | |
| 252238 | 10/1988 | Japan ........................................... | 73/9 |
| 106456 | 4/1992 | Japan ........................................... | 73/9 |
| 879391 | 11/1981 | U.S.S.R. ..................................... | 73/9 |
| 1601560 | 10/1990 | U.S.S.R. ..................................... | 73/9 |
| 2121970 | 1/1984 | United Kingdom . | |

OTHER PUBLICATIONS

Abstract of Japanese Patent No. 62–280636. Patent Abstracts of Japan. Vol. 12, No. 166. (Dec. 5, 1987) p. 704.

*Primary Examiner*—Hezron E. Williams
*Assistant Examiner*—Nashmiya Ashraf
*Attorney, Agent, or Firm*—Browdy and Neimark

[57] ABSTRACT

A process for measuring the friction and the coefficient of friction of sheet-shaped materials (layer materials), espeically paper. This process is characterized in that a test surface of the material and a conter-surface of a material, in relation to which it is desired to measure the friction, in said testing process are loaded with a normal (transverse) force which is applied against the test surface of the sheet-shaped material, the position of said normal force in the space being maintained essentially stationary in the testing process, and a friction force acting in the direction of the tested surface, and determining the combination of firction force acting in the direction of the test surface and normal force, which can be applied without mutual movement (sliding) or are required respectively, for sliding movement between the test surface and the counter-surface, for determining a resting friction (static friction) and a sliding friction (kinetic friction) between the test surface and the counter-surface.

5 Claims, 2 Drawing Sheets

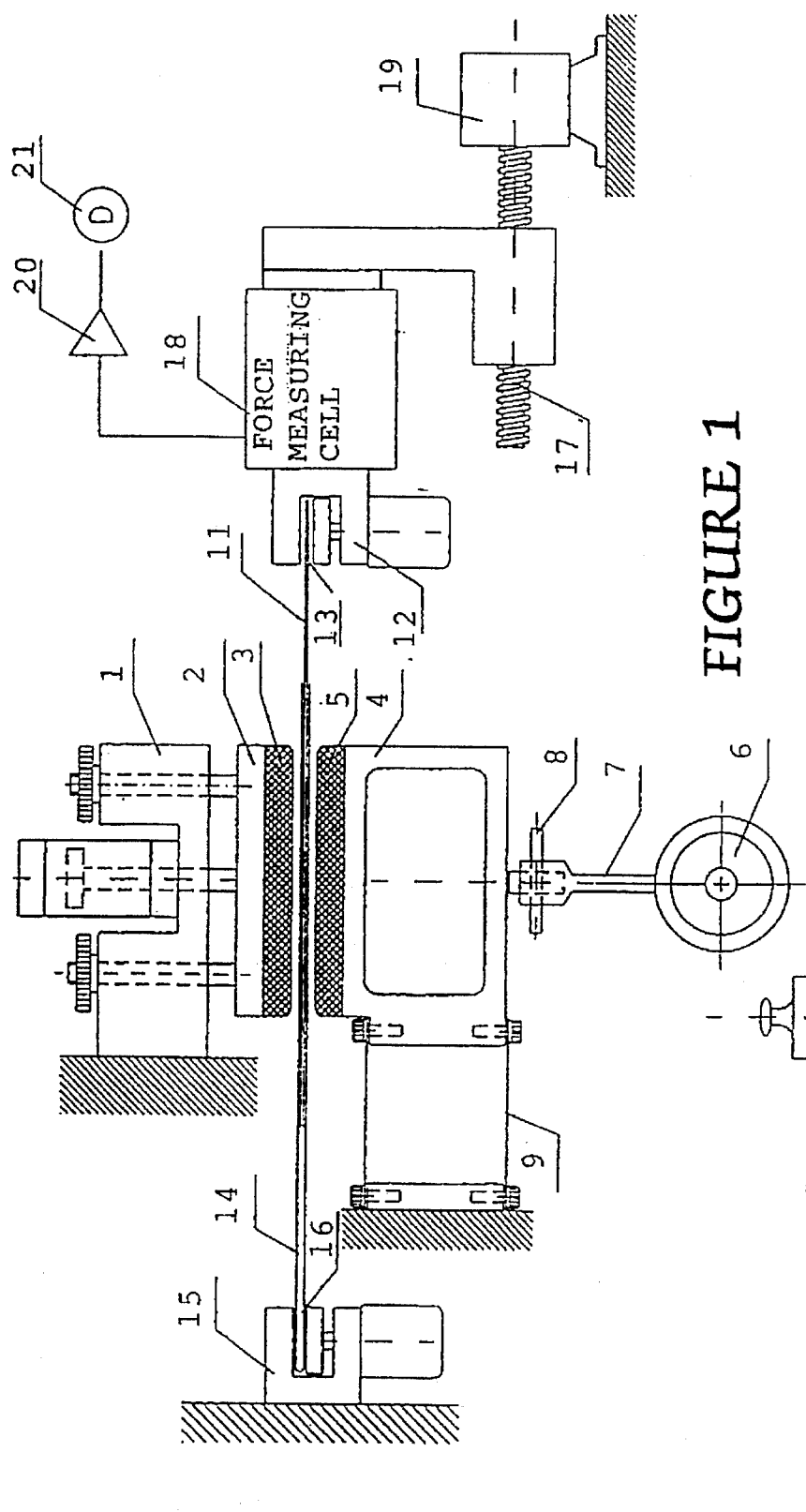
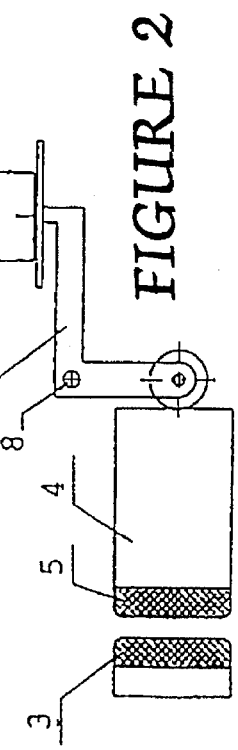
FIGURE 1
FIGURE 2

PROCESS AND A DEVICE FOR MEASURING STATIC AND DYNAMIC FRICTION OF SHEET-SHAPED MATERIALS

BACKGROUND OF THE INVENTION

1. Technical Field of the Invention

This invention is related to a process for measuring the friction and determining the coefficient of friction of sheet-shaped materials, especially paper and similar materials, especially based on cellulose, e.g. from wood, such as softwood or hardwood, but also paper from other kinds of cellulose materials and also paper from other materials as well as other sheet-shaped materials of organic or inorganic materials, also including metals or similar materials, as well as plastics, elastomers, fabrics, such as woven or non-woven fabrics, etc.

The expressions "sheet", "sheet-shaped" and "layer" herein is on the first hand intended to comprise a body having an extension in one direction which is small, preferably at most 1:5, especially at most 1:10, in relation to the extension thereof in two thereto and in relation to each other perpendicular directions.

According to this invention it is possible to determine the friction of a sheet-shaped test material, such as a sheet, against another sheet-shaped material or the same kind of sheet-shaped material, but also against a material with another shape than the sheet-shape, e.g. a piece of metal, plastics, elastomeric material, etc., having a suitable shape.

In the following the surface of the test material having sheet-shape is usually only called "test surface" and the surface of the material against which the friction is measured is called "counter-surface" but alternatively the material of a friction surface forming body which does not exhibit "sheet-shape" can be the material for which the friction against various other materials is to be determined.

2. Prior Art

A common way of determining the friction against a sheet-shaped material is according to the level of the prior art to arrange the sheet-shaped material on a flat surface acting as a support for the sheet-shaped material, and measuring the force which is required for bringing a counter-surface forming body having a known weight to move on the surface of the sheet-shaped material. The transverse or force which said body exerts against the surface (especially the normal force, i.e. a force acting in a direction normal or perpendicular to said surface) depends on the weight of the body under the influence of the gravity force. The sheet-shaped material can be arranged on a supporting surface, the plane of which can be tilted in a degree which is required for bringing the counter-surface forming body to start moving on said surface by the influence of the gravity force component acting in the direction of the plane of said surface, whereby the slope of said plane against the horizontal plane when the body starts sliding gives a measure of the force of friction and coefficient of friction in question, or else the body can be pulled on the preferably horizontally arranged surface of the sheet-shaped material and the pulling force and normal force and preferably also the surface load are measured when the body starts to slide. Said previously known methods have, however, substantial disadvantages caused e.g. by uneven load of the force of friction, the appearance of jumping movement of the body, the creation of acceleration forces which disturb the measurement of the force of friction, that the application of the normal force may take place under a sidewise movement of the normal force and that the application of the normal force may take place with jumps or with variations from one experiment to the other, and the measuring methods are often time-consuming and complicated, etc.

It has now surprisingly been revealed that it is possible to completely or to an extential degree eliminate said deficiencies and also to simplify the measurement with the process and the device according to this invention.

OBJECT AND SUMMARY OF THE INVENTION

When performing friction measurements of the kind mentioned above the position of the transverse, especially normal forces exerted on the sheet-shaped material is according to this invention maintained essentially stationary. This permits the point (area) of action of said forces to optionally be displaced in a direction which is perpendicular to the friction surface, e.g. in case a supporting substrate for said sheet material is elastically resilient and compressible when subjected to said normal forces. The area within which the normal force or forces act is, on the contrary, preferably not at all or only to a slight degree displaced in a direction which is perpendicular to the normal forces. This is a part from the movement caused by elastic deformation and apparatus play which may take place when applying a friction measuring force on the friction surface of the sheet material, i.e. on the surface area subjected to the normal force, in the direction of the plane of the friction surface. According to the invention it is also preferred that the test material can be moved only in a direction in its surface plane by a force, especially a tensile force, which is exerted on the test material and acts in a direction in its surface plane when measuring the friction. This can be achieved by having the test material clamped in one or more clamping means (clamping jaws) during the testing procedure. The clamping devices should be arranged so that the tested material sample moves in the direction of the friction measuring force only, i.e. usually in the direction of a tensile force applied to the sample. This can be achieved by arranging the movable clamping means movable along a straight line or movement axis, the extension of said line preferably lying in or passing very close to the plane of the test surface or counter-surface and in parallel or very closely to parallel with said surfaces. This can be achieved by clamping the test sample and/or the counter-surface material piece e.g. in the shape of strip or strips, rigidly in the clamping device or devices, especially the movable clamping device or devices, and especially against movements or movement components which deviate from the straight line movements of the clamping devices, such as a rotating movement component in the plane of the friction surface/counter-surface. This can be achieved e.g. by using a test sample or counter-surface sample respectively with a sufficient breath, e.g. about 50 mm, e.g. for paper and materials, especially fibrous materials, which have a stiffness which is sufficient for preventing the deviating movement mentioned above at least to an extent which is sufficient for a reliable friction measurement based on a straight line movement of the test surface and/or counter-surface respectively as mentioned above, especially along the extension of a straight line movement of a sample clamping device. Thus, in order to obtain said desired testing conditions the clamping devices 12, 15 on the figure should normally be "stiff" and not flexible or tiltable, i.e. force the test sample surface and/or counter-surface to perform a straight line movement.

Furthermore, it is important that the shape of the device prevents that the tested material alternating sticks and performs jump movements. To this contributes also that the upper tested material can have a low mass which counteracts the influence of the mass forces on the measurement. Furthermore, the tested material can have a very small thickness which makes it possible to apply the tensile forces very close to the tested material sheet so that the formation of bending momentum or force components perpendicular to the test surface acting on the tested sample is counteracted.

For the friction measurement the sheet material is thus subjected to forces (friction measurement forces), especially tensile forces, especially such forces which are large enough to cause the appearance or disappearance respectively of a movement or a beginning or continuous, even movement (slide) of the test material (sheet-shaped material) in relation to the counter-surface material.

The size of said friction forces can be measured and registered e.g. with a strain gauge (wire strain gauge). The transfer (the coupling) of the force from the means or device exerting or applying the friction measuring force to the sheet material can be more or less elastic. Usually it is suitable or acceptable that said coupling (transfer) when measuring the static friction is more elastic than when measuring the kinetic friction. The elasticity of the force transfer may be made variable for an adaption to the type of friction. It is suitable to use clamping devices in which the sheet-shaped material is clamped, e.g. between clamping jaws, at least one of said clamping devices being arranged displaceable in a direction which makes it possible to exert a force on the sheet-shaped material in the direction of the area of the sheet within which the friction measurement is performed, especially a tensile force.

The sheet-shaped material is preferably used in the testing process in the shape of strips which are arranged between the opposite loading surfaces with at least one end of the strip extending outwards from said surfaces so that the strip can be clamped in the movable clamping means for exerting a force in the direction of the friction surface (the friction measuring force). According to a suitable embodiment the load surfaces are arranged in the vertical direction or sloping in relation to the horizontal plane so that the sheet-shaped tested material, preferably in the shape of a strip, can easily be inserted into the gap between said surfaces under the influence of the gravity force, in which case preferably also the gap between the clamping means of the movable clamping device are directed parallel to the gap between the load surfaces, as is preferably also the gap between the clamping means in one or more optionally used further clamping devices used for clamping of a further sheet-shaped material (counter-surface material) used in the testing process.

In the testing process also the counter-surface material may suitably be sheet-shaped and used e.g. in the shape of a strip. The counter-surface material may e.g. be the same kind of material as the tested material, e.g. paper. A strip of the sheet-shaped material having one end clamped in a movable, tensile force exerting clamping device, may in the gap between the load surfaces be arranged between two other pieces, preferably two strips or a double-folded strip of the sheet-shaped counter-surface material, in which case said counter-surface material is suitably maintained stationary between the load surfaces, e.g. by holding an extending end of the counter-surface material or pieces in a stationary (immovable) clamping device. This permits a simple way of measuring the friction of e.g. paper against the same kind of paper. The paper web direction (machine direction) of the tested material and the counter-surface material may then be directed in the same direction, directed 90° in relation to each other, 180° in relation to each other, or in other mutual directions, etc. and with various combinations of the upper sides and the lower sides (wire sides) of said sheets applying against each other. When performing the measurement one may either apply a normal force of a constant size against the friction surfaces of the sheet material and the counter-surface material and vary the friction measuring force in the direction of the friction surface, or apply a constant friction measuring force and vary the normal force until a sliding movement appears or disappears respectively.

For measuring the friction against only one of the surfaces of the sheet-shaped material it is also possible to arrange one of the opposite load surfaces movable in the direction of the friction surface plane, preferably with the lowest possible friction and preferably friction of a known size, e.g. by arranging the movable load surface displaceable on roller bearings or similar devices.

It is usually also essential that the load surfaces which exert a normal force against the sheet-shaped material are guided so that they are maintained parallel to each other and preferably also to the sheet-shaped tested material and apply a load force (normal force) perpendicular to the sheet-shaped material, and especially to prevent that the load surfaces exert a sizing or gripping effect on the sheet-shaped material by the influence of a tensile force applied in the direction of the sheet, i.e. that the tensile force applied for measuring the friction creates a normal force component. The risks for this can be decreased by applying the friction force in the plane of the friction surface.

It is usually essential that the load surfaces are made from an elastic material, especially a layer of elastic material on a preferably plane substrate of a rigid material, such as a metal, so that an evenly distributed contact pressure on the sheet-shaped material is obtained.

Furthermore, it is an advantage if the tested material, especially the test strip, can move only in the direction of the applied tensile force and that sliding in other directions is efficiently prevented, suitably by rigid clamping in clamping devices in the measuring process. The apparatus should, furthermore, as far as possible prevent that the surfaces alternating are sized and alternating make jump-like movements, so-called stick-slip movement.

It is also important that the tested material and optionally the counter-surface material are of small thickness so that the tensile force (the friction force) can be applied in a direction close to or in the plane of the friction surface, and also so that bending movements on the tested material are avoided or decreased. A thickness of below 2 mm, usually below 1 mm or below 0.5 mm, e.g. below 0.2 mm is often a value which gives good testing conditions, e.g. when testing paper (including also board, paperboard and similar).

According to the invention it is possible to use test pieces or samples with a very low weight which makes it possible to decrease the influence of the mass forces on the friction measurement. When using a strip-shaped test sample material the strips may e.g. have a length of at most 300 mm, e.g. at most 200 mm or at most 100 mm, and a minimum length which is determined by the apparatus, usually at least 20 mm or at least 50 mm, in each case as single or double-folded material, and the bredth may often be at most 100 mm or at most 75 mm, usually down to at least 5 mm or at least 10 mm or at least 25 mm, e.g. a bredth of about 50 mm, e.g. 150×50 mm or 300×50 mm, double-folded to half the length, which is often suitable for paper.

A further advantage of the invention is that the tested material samples may be produced uncomplicated and efficiently, e.g. by cutting, punching or stamping of strips of the sheet-shaped material, and that the test samples can easily be introduced into the testing apparatus without touching the contact surfaces (friction surfaces) during the handling.

It is usually also suitable that the normal force, which acts between the surfaces which are subjected to friction measuring, is applied under controlled conditions. Usually a gradual increase of the normal force is desired, wherein the friction surfaces are brought together without mutual sliding movement. Furthermore, it is essential to control the period of time during which the normal force acts upon the friction surfaces before the measurement is performed.

When measuring the friction of such materials as paper and similar it is often essential that the friction measurement is performed a repeated number of times on the same surfaces in order to obtaining a stable and reproducable result.

BRIEF DESCRIPTION OF THE DRAWINGS

On the enclosed drawing the Figures disclose:

FIGS. 1 and 2 an example of an apparatus which can be used for carrying out the process according to this invention;

Figure 3:
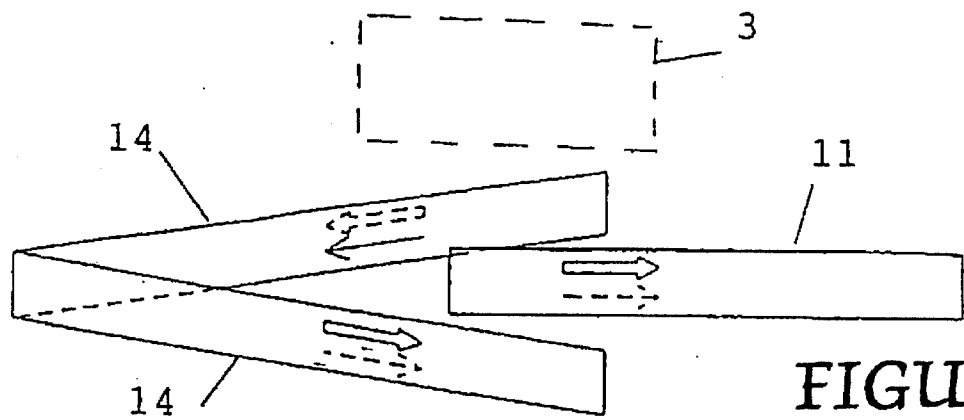
Figure 4:
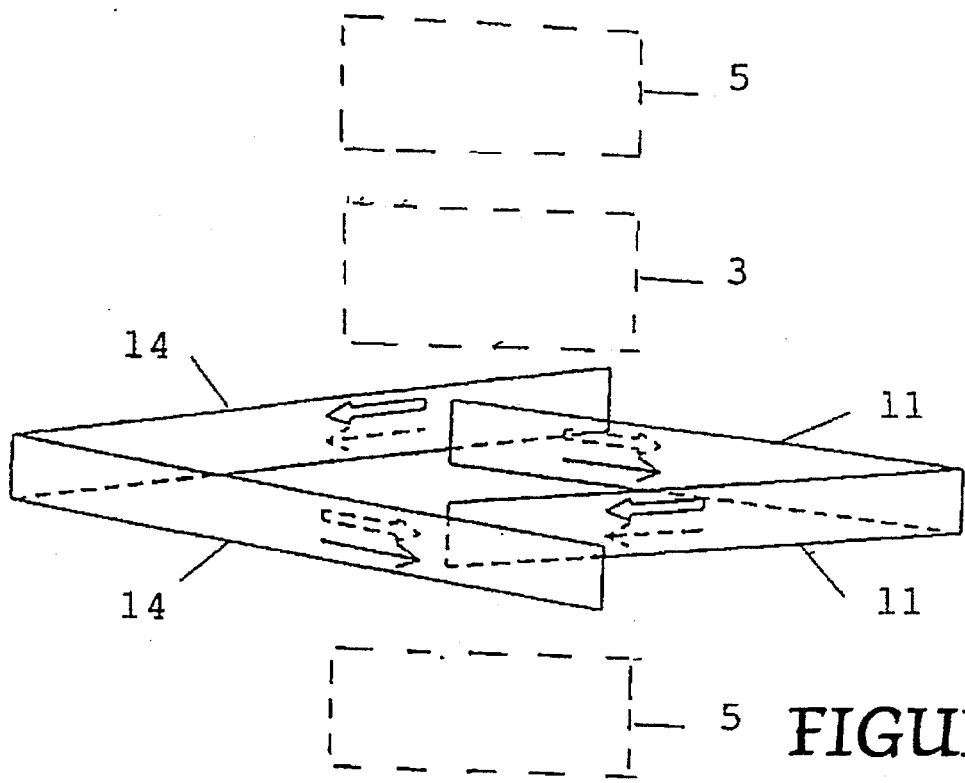

on FIGS. 3 and 4 examples of the arrangement of double or simple strips of sheet-shaped material, e.g. paper, which exhibit varying characteristics in different directions.

DETAILED DESCRIPTION OF THE PREFERRED EMBODIMENTS OF THE INVENTION

FIG. 1 discloses a normal force loading apparatus 1 with a fixed (during measurement) normal force applying means 2 with a layer 3 of an elastic material, which forms one of the load surfaces, and a movable and force applying normal force applying means 4 with a layer 5 of an elastic material, which forms the other load surface. The load applying means 2 which is fixed during the measurement may also be movable (displaceable) from the opposite force applying means 4 to a charging position in which charging (inserting) of the sheet-shaped material between the force applying means 2,4 is simplified, and back towards the opposite force applying means 4 to a fixed measurement position in which the fixed force applying means 2 is loaded with (subjected to) the normal force exerted by the movable force applying means 4. The normal force is according to the embodiment disclosed on the Figure, in which both load surfaces are vertically directed, obtained with a weight 6 which by a lever 7, which is pivoted around a horizontal axis 8, transfers the gravity force redirected into the horizontal direction to the movable force applying means 4, which is held by thin blade springs 9. A strip 11 of a sheet-shaped material is arranged between the elastic layers 3 and 5 respectively of the force applying means 2 and 4 respectively, and one end of the strip 11 is clamped into a movable tensile force applying means 12 in a gap 13 between clamping means (clamping jaws). The counter-surface material consists of a double-folded strip 14 of a sheet-shaped material, and the test material strip 11 is arranged between the two legs thereof. The end of the strip 14 is clamped in a fixedly arranged clamping device 15 in a gap 16 between clamping means. The test material may, however, alternatively consist of two single strips 11 laid tight together or of a double-folded strip and in both embodiments be arranged between the two layers of a counter-surface material 14. The tensile force acting as friction measuring force is exerted on the movable clamping device 12 by a tensile force device 17, outlined as a screw-nut device, with a driving means 19, shown as a motor which turns said screw. The tensile means device is through a force measuring cell 18, e.g. a wire strain gauge, connected to the force applying device 12. Signals from said measuring cell 18 are, through a calculating unit 20, transferred to a display-printer device 21. The measured values of the normal force and friction measuring force are used for calculating the coefficient of friction of the surfaces in question at the load condition in question.

FIGS. 3 and 4 disclose in outline an example of the mutual relation between test strips 11 and counter-surface strips 14 of sheet-shaped material with characteristics which differ in various surface plane directions, typically paper, which was made in a paper-making machine and which discloses a "machine direction" and an "upper side" and a "lower side" which last-mentioned side faced a wire cloth or similar. The direction of the arrows shows the machine direction, and the arrow with a double line shows the upper side and the arrow with a single line the lower side, and full lines relate to surfaces turned towards the viewer and hatched lines surfaces turned from the viewer, respectively FIG. 3 corresponds to the test and counter-surface materials arrangement disclosed on FIG. 1.

FIG. 4 discloses corresponding conditions when also the test material exhibits double legs, in this case a double-folded strip.

As is immediately obvious also a number of other combinations of directions and sides can be achieved, wherein the machinery direction may also be directed in an angle in relation to the longitudinal direction of the strip, 90°.

The apparatus disclosed above has been used with good results for measuring the friction of writing paper, copying paper, sack craft paper, fibre board for corrugated fibre board, etc. against the same kind of material and against other kinds of material, such as aluminum, iron, polyethylene plastics, etc., and of metals, such as steel, aluminum, brass, etc., plastics, such as polyethylene, polyamides, polyesters, cloth, such as cotton, polyester, etc. against the same material and against other of the materials mentioned above, wherein measuring values with a low degree of spread was obtained.

I claim:

1. A process for measuring friction of paper surfaces against paper surfaces for determining a coefficient of friction between said surfaces, which comprises arranging paper friction testing samples with contacting plane friction test surfaces between two mutually parallel opposite plane load surfaces, exerting with the aid of said load surfaces, an evenly distributed contact force on the friction test surfaces of the paper samples in a direction essentially normal to the friction test surfaces, maintaining a first of said samples and the load surfaces stationary, exerting a friction measuring tensile force on a second of said paper samples, the friction testing surfaces of which are in contact with the friction testing surfaces of said first sample, said tensile force being exerted with movable paper sample clamping means arranged for being moved in a direction of a straight line and for clamping said second paper sample for movement along the straight line which is in a direction of the friction test surfaces when measuring the friction, and measuring the combination of said essentially normal force, exerted with the aid of the load surfaces on the paper friction test surfaces, and said tensile force, which is required for a sliding movement of the friction test surfaces of said clamped second paper friction test sample relative to the contacting paper surfaces of said first paper friction test sample for determining said coefficient of friction.

2. A process according to claim 1 wherein the paper friction test samples consist of paper strips with a breadth of at least 10 mm.

3. A process according to claim 1 wherein one of the essentially normal force exerted on the paper friction test surfaces and the tensile force acting on the second paper friction test sample is gradually changed so that sliding (movement) or rest (non-movement) of the friction test surfaces of the second friction test sample in relation to the first test sample is obtained.

4. A friction measuring apparatus for carrying out the process according to claim 1 which apparatus comprises a loading device with said two mutually opposite plane load surfaces, of which at least one is movable in a direction which is transverse to said plane load surfaces for applying under controlled conditions, said essentially normal force perpendicular to said paper friction test surfaces arranged between said load surfaces, said loading device being arranged with the load surfaces stationary, apart from movability in directions transverse to the load surfaces, said apparatus being provided with means for holding said first paper friction test sample stationary together with the load surfaces, and at least one said clamping means, which is movable in the direction of said straight line and arranged for holding said second paper friction test sample clamped and for moving said second paper friction test sample between said load surfaces in a straight line parallel to said plane load surfaces and parallel to the direction of movement of the clamping means, by exerting said tensile force on said second paper friction test sample, and means for controlling and measuring the essentially normal force exerted by the load surfaces against the paper friction test surfaces and the tensile force exerted by the movable clamping means on the second paper friction test sample.

5. An apparatus according to claim 4 wherein said samples are strip-shaped paper friction test samples, and said clamping means comprise clamping jaws for holding the strip-shaped samples at one end thereof.

* * * * *